(12) United States Patent
Zhao et al.

(10) Patent No.: US 8,946,469 B2
(45) Date of Patent: Feb. 3, 2015

(54) PROCESS FOR PREPARING ISOPIMARIC ACID

(75) Inventors: Zhendong Zhao, Jiangsu (CN); Xingdi Li, Jiangsu (CN); Liangwu Bi, Jiangsu (CN); Yuxiang Chen, Jiangsu (CN); Yan Gu, Jiangsu (CN); Dongmei Li, Jiangsu (CN); Jing Wang, Jiangsu (CN)

(73) Assignee: Institute of Chemical Industry of Forest Products, Chinese Academy of Forestry, Nanjing, Jiangsu (CN)

( * ) Notice: Subject to any disclaimer, the term of this patent is extended or adjusted under 35 U.S.C. 154(b) by 172 days.

(21) Appl. No.: 12/927,097

(22) Filed: Nov. 4, 2010

(65) Prior Publication Data

US 2011/0060160 A1    Mar. 10, 2011

Related U.S. Application Data

(63) Continuation of application No. PCT/CN2009/072160, filed on Jun. 5, 2009.

(30) Foreign Application Priority Data

Jun. 6, 2008  (CN) .......................... 2008 1 0123831

(51) Int. Cl.
C07C 61/29 (2006.01)
C07C 51/43 (2006.01)

(52) U.S. Cl.
CPC .................. *C07C 61/29* (2013.01); *C07C 51/43* (2013.01); *C07C 2103/22* (2013.01)
USPC ....................................................... 562/404

(58) Field of Classification Search
None
See application file for complete search history.

(56) References Cited

FOREIGN PATENT DOCUMENTS

| CN | 101302151 A | 11/2008 |
|---|---|---|
| FR | 1509992 A | 1/1968 |
| WO | WO 2009/146659 A1 | 10/2009 |

OTHER PUBLICATIONS

Baldwin et al. (J. Org. Chem., 1958, 23(1), 25).*
Harris et al. (2) (J. Am. Chem. Soc., 1948, 70(1), 2079).*
http://www.chemindustry.com/chemicals/0300726.html).*
Wenkert et al.(J. Am. Chem. Soc., 1958, 2912).*
Green et al. (J. Chem. Soc., 1958, 4715).*
STN abstract of Li et al. (Linchan Huaxue Yu Gongye, 2008, 28(5), 21).*
Zhao et al. (Acta Crystallographica, Section E: Structure Reports Online, 2009, 65(6), o1429).*
STN abstract of Zhao et al. (Acta Crystallographica, Section E: Structure Reports Online, 2009, 65(6), o1429).*
George, et al. Resin Acids. III. The Isolation of Dextropimaric Acid and a New Pimaric-type Acid, Isodextropimaric Acid., J. Am. Chem. Soc., 1948, pp. 2079-2081, vol. 70, No. 1.
PCT International Search Report, PCT/CN2009/072160, dated Sep. 10, 2009.
Li et al., New Process for Isolation and Preparation of Isopimaric Acid, Aug. 2008, pp. 2-25, vol. 28, No. 5.
Sun, Shuguang, Improved Process for separating Levopimaric acid, Communications of Chemical Industry of Forest Products, 1992, pp. 20-21, No. 3.
Baldwin et al., A New Method for Isolating Isodextropimaric Acid from Pine Oleoresin and Rosin, Contribution from the Naval Stores Research Section, U.S. Department of Agriculture, Jan. 1958, pp. 25-26, vol. 23.

* cited by examiner

*Primary Examiner* — Rosalynd Keys
*Assistant Examiner* — Jennifer C Sawyer
(74) *Attorney, Agent, or Firm* — TraskBritt, P.C.

(57) ABSTRACT

Disclosed is a process for preparing isopimaric acid, comprising the following steps: First step: dissolving thermally isomerized rosin in acetone, adding in drops a solution of isobutanolamine in acetone to form a precipitate, standing, filtering, washing with ethanol, and drying to obtain crude ammonium salt of isopimaric acid; recrystallizing the crude ammonium salt of isopimaric acid according to multi-recrystallization, and drying to obtain purified crystal of ammonium salt of isopimaric acid; Second step: dissolving the purified crystal of ammonium salt of isopimaric acid obtained in the first step in ether, adding hydrochloric acid in portions until the crystal of ammonium salt of isopimaric acid disappears, removing a water layer and washing the ether layer with water to neutral, evaporating the ether, dissolving the residue in acetone, adding water slowly into the solution dropwise until crystals cease to grow, then filtering and drying to obtain purified isopimaric acid.

6 Claims, 4 Drawing Sheets

PROCESS FOR PREPARING ISOPIMARIC ACID

CROSS-REFERENCE TO RELATED APPLICATIONS

This application is a continuation of PCT International Patent Application No. PCT/CN2009/072160, filed on Jun. 5, 2009, designating the United States of America, and published as PCT International Publication No. WO 2009/146659 A1 on Dec. 10, 2009, which application claims priority under Article 8 of the Patent Cooperation Treaty to Chinese Patent Application No. 200810123831.2 filed on Jun. 6, 2008, the contents of the entirety of each of which are hereby incorporated hereby by this reference.

FIELD OF THE INVENTION

The present invention relates to a process for preparing isopimaric acid, which is an important component of rosin or pine oleoresin.

BACKGROUND OF THE INVENTION

Isopimaric acid is an important component of rosin or pine oleoresin. Its content in *Pinus elliottii* rosin is about 20%. The stable phenanthrene ring skeleton structure and unique exocyclic double bond of isopimaric acid endow it with multiple characteristics of chemical reactions. Therefore, separating and purifying isopimaric acid from typical pine oleoresin or rosin is important for the development and utilization of pimaric-type resin acids.

There are three known isodextropimaric acid, which is an isomer of isopimaric acid, separating and purifying methods: the "piperidine precipitation method," the "maleic anhydride addition-isobutanolamine precipitation method" and the "distillation method". In a report of Loeblich et al., isodextropimaric acid is separated by direct piperidine precipitation method and the yield of isodextropimaric acid is 4.7% (V. M. Loeblich and R. V. Lawrence, "A New Method for Isolating Isodextropimaric Acid From Pine Oleoresin and Rosin," *J. Org. Chem.* 23(1):25-26 (1958)). This method directly separates the ammonium salt of isodextropimaric acid from raw material of rosin and the operation is simple. Its shortcoming is that although piperidine is selective to isodextropimaric acid, the crystallization rate of the generated ammonium salt of isodextropimaric acid is very low, the production cycle is long and the yield is low. Harris et al. removed abietic acid-type resin acids through a Diels-Alder addition reaction of maleic anhydride and then obtained isodextropimaric acid through selective precipitation of isobutanolamine. The yield of isodextropimaric acid is 8% (G. C. Harris and T. F. Sanderson, "Rosin Acids (III). The Isolation of Dextropimaric Acid, A New Pimaric-Type Acid, Isodextropimaric Acid," *J. Am. Chem. Soc.* 70(1):2079-2085 (1948)). In this method, it is difficult to separate maleopimaric acid and unreacted resin acids (including pimaric-type resin acids, dehydro-abietic acid and a small amount of abietic acid-type resin acid that is not thoroughly reacted), and the separated unreacted resin acids may contain maleopimaric acid. Harris et al. also adopted a distillation method to directly evaporate pimaric acid and isodextropimaric acid and then used isobutanolamine to separate isodextropimaric acid. The yield relative to rosin is 4% (G. C. Harris and T. F. Sanderson, "Rosin Acids (III). The Isolation of Dextropimaric Acid, A New Pimaric-Type Acid, Isodextropimaric Acid," *J. Am. Chem. Soc.* 70(1): 2079-2085 (1948)). This method has a high requirement for fractionation conditions; in addition, the operation is not easy and the yield of isodextropimaric acid is low.

At present, there are few domestic reports on the research of the separation and purification of isopimaric acid and no industrial-grade high-purity isopimaric acid products. Therefore, the exploration on the methods for separating isopimaric acid with high efficiency, high yield and high economic feasibility will accelerate the application of isopimaric acid in medical, biological, material and other fields.

SUMMARY OF THE INVENTION

In order to solve the shortcomings of the prior art, which has high costs and low yields in the preparation of isopimaric acid, the present invention provides a process for preparing isopimaric acid. The process is characterized by low production costs, high yield and high purity of isopimaric acid product, as high as 95%.

The present invention mainly adopts the following technical route:

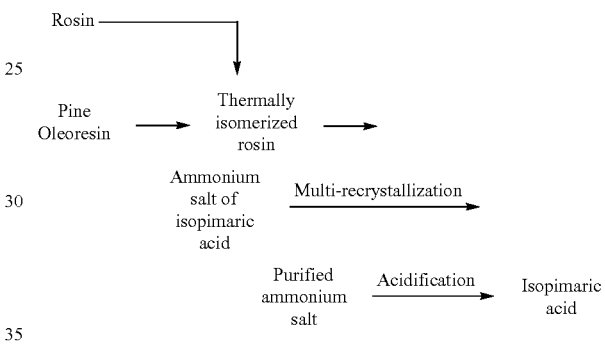

The technical scheme of the present invention is a process for preparing isopimaric acid, including the following steps:

Step 1: Dissolve thermally isomerized rosin in acetone with a mass of one to ten times, add in drops of an acetone solution of isobutanolamine with a mass equivalent to 1%~40% of the mass of thermally isomerized rosin (acetone/isobutanolamine=1:1 mL/g) to form precipitation, let stand, filter, wash with 50% (v/v) ethanol, and dry to obtain crude ammonium salt of isopimaric acid; recrystallize each group of crude ammonium salt of isopimaric acid for five times according to multi-recrystallization and dry to obtain purified crystal of ammonium salt of isopimaric acid. The solvent used in multi-recrystallization method is any selected from the group of 95% (v/v) ethanol, methyl acetate, methyl acetate-anhydrous ethanol, anhydrous ethanol and methanol.

Step 2: Dissolve the purified crystal of ammonium salt of isopimaric acid obtained in the first step in ether with a mass of one to twenty times, add 1 wt %~20 wt % hydrochloric acid in batch until the crystal of ammonium salt of isopimaric acid disappears, remove the water layer and wash the ether layer with water to neutral, evaporate ether at one atmosphere (1 atm) and 30° C.~50° C., dissolve the residue in acetone with a mass of 0.5~5 times, slowly add water in drops into the solution until precipitated crystals cease to grow, filter and dry to obtain purified isopimaric acid.

Wherein, the thermally isomerized rosin is prepared by the following method: evaporate a little amount of water from pine oleoresin containing isopimaric acid at one atmosphere and 90° C.~114° C., then evaporate turpentine at 10 kPa~50 kPa and 140° C.~170° C., then raise temperature to 150° C.~180° C. to take isomerization reaction for one hour to approximately three hours, filter and cool to room temperature to obtain thermally isomerized rosin. The said pine oleoresin containing isopimaric acid is any one of the group of *Pinus elliottii* pine oleoresin, *Pinus caribaea* pine oleoresin, *Pinus khasya* pine oleoresin and *Pinus massoniana* pine oleoresin, wherein the best preference is *Pinus elliottii* pine oleoresin. The said rosin may be gum rosin, pamite or wood rosin, wherein *Pinus elliottii* rosin, *Pinus caribaea* rosin, *Pinus khasya* rosin or *Pinus massoniana* rosin among gum rosin is preferred, and the best preference is *Pinus elliottii* rosin.

The technical effect of the present invention is as follows:

After pine oleoresin being undertaken distillation of turpentine and thermal isomerization of rosin, most of the levopimaric acid is isomerized into abietic acid-type resin acids. As both levopimaric acid and isopimaric acid may react with isobutanolamine or piperidine after thermal isomerization, only isopimaric acid is retained and the reaction yield is raised. The yield, with respect to thermally isomerized rosin in the process, provided in the present invention may reach 10.1%.

Ammonium salt of isopimaric acid adopts 95% (v/v) ethanol as solvent. According to multi-recrystallization, each group of crystal is recrystallized for five times. This procedure can effectively remove other resin acids contained in ammonium salt of isopimaric acid, in particular abietic acid. In this way, the interference of other resin acids and the loss of ammonium salt of isopimaric acid are minimized to an extreme and the purity of isopimaric acid is raised to greater than 95%.

In comparison with the piperidine method, the crystallization rate of isobutanolamine to isopimaric acid in the process provided in the present invention is higher than the crystallization rate of piperidine to isopimaric acid, so the process significantly reduces separation time and saves organic amine. Compared with maleic anhydride addition, isobutanolamine precipitation method, this process directly separates isopimaric acid from rosin, reduces the loss due to intermediate steps, raises the yield of isopimaric acid and simplifies operation steps. Compared with a distillation method, this method has a lower requirement for the operating conditions and has a higher yield.

BRIEF DESCRIPTION OF THE DRAWINGS

In FIG. 1, "C" refers to crystallization, "A" refers to the "useful mother liquor," which is left after filtration and crystallization and will be merged and used in the next crystallization process, and mother liquor refers to the part that is no longer used and will be discarded.

DETAILED DESCRIPTION OF THE EMBODIMENTS

Figure 1:
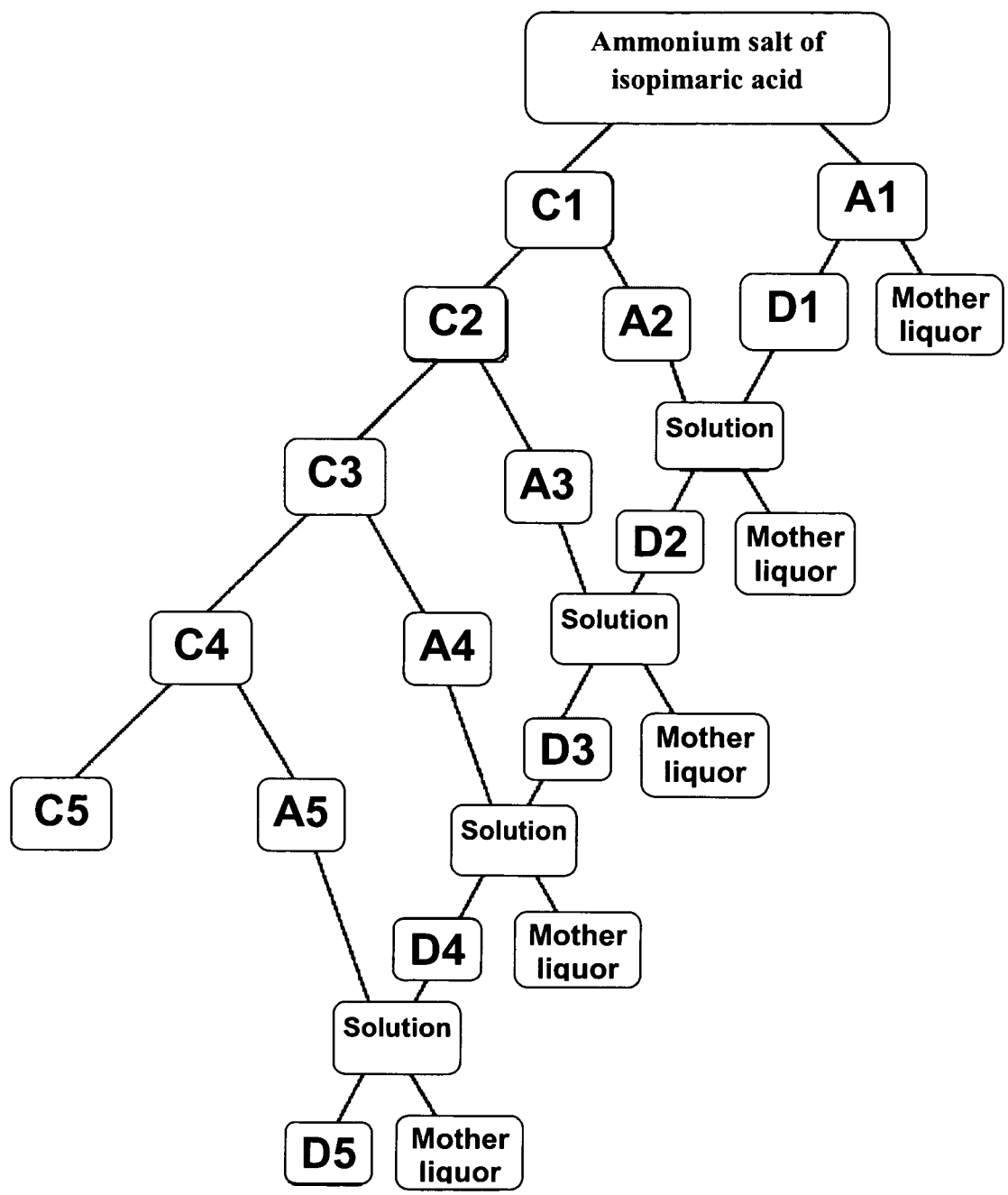
FIG. 1 is an operation flow chart of the multi-crystallization method of the present invention.

The present invention will be further described in connection with examples.

Example 1

A process for preparing isopimaric acid, including the following steps:

Step 1: Dissolve thermally isomerized rosin in acetone with a mass of 1 to 10 times, add in drops of an acetone solution of isobutanolamine with a mass equivalent to 1%~40% of the mass of thermally isomerized rosin (acetone/isobutanolamine=1:1 mL/g) to form a precipitate, let stand, filter, wash with 50% (v/v) ethanol, and dry to obtain crude ammonium salt of isopimaric acid; recrystallize each group of crude ammonium salt of isopimaric acid for five times according to multi-recrystallization and dry to obtain purified crystal of ammonium salt of isopimaric acid. The solvent used in the multi-recrystallization method is any one selected from the group of 95% (v/v) ethanol, methyl acetate, methyl acetate-anhydrous ethanol, anhydrous ethanol and methanol. The amount of acetone may be 1, 3 or 10 times of the mass of thermally isomerized rosin. The amount of the isobutanolamine added in drops may be 1%, 22% or 40% of the mass of thermally isomerized rosin.

Step 2: Dissolve the purified crystal of ammonium salt of isopimaric acid obtained in the first step in ether with a mass of 1 to 20 times, add 1 wt %~20 wt % hydrochloric acid in batches until the crystal of ammonium salt of isopimaric acid disappears, remove the water layer and wash ether layer with water to neutral, evaporate ether at one atmosphere (1 atm) and 30° C.~50° C., dissolve the residue in acetone with a mass of 0.5~5 times, slowly add water in drops into the solution until precipitated crystals cease to grow, filter and dry to obtain purified isopimaric acid. The amount of ether may be 1, 11 or 20 times of the mass of ammonium salt of isopimaric acid. The concentration of hydrochloric acid may be 1 wt %, 10 wt % or 20 wt %.

Example 2

Put 600 g *Pinus elliottii* pine oleoresin into a 1 L four-neck flask, install a thermometer, a distilling head, a Y-tail pipe and a receiving flask, input nitrogen, evaporate a little amount of water contained in *Pinus elliottii* pine oleoresin at one atmosphere (1 atm) and 90° C.~114° C., evaporate turpentine at 10 kPa~50 kPa and 140° C.~170° C., raise temperature again to 150° C.~180° C. to take isomerization reaction for 1 hour~3 hours, filter and cool to room temperature to obtain 478 g thermally isomerized rosin. Take samples, undergo methyl esterification and then perform gas chromatography (GC) analysis. In the thermally isomerized rosin, the mass fraction of isopimaric acid is 23.75%.

Example 3

*Pinus elliottii* pine oleoresin in Example 2 is changed into *Pinus caribaea* pine oleoresin and the rest is unchanged.

Example 4

*Pinus elliottii* pine oleoresin in Example 2 is changed into *Pinus khasya* pine oleoresin and the rest is unchanged.

Example 5

*Pinus elliottii* pine oleoresin in Example 2 is changed into *Pinus massoniana* pine oleoresin and the rest is unchanged.

Example 6

Isomerize 200 g of gum rosin, which may be *Pinus elliottii* rosin, *Pinus caribaea* rosin, *Pinus khasya* rosin or *Pinus massoniana* rosin, at 150° C.~180° C. for 1 hour~3 hours, filter and cool to room temperature to obtain thermally isomerized rosin.

Example 7

Dissolve 200 g thermally isomerized rosin obtained from Example 2 in acetone with the same mass, add in drops of the acetone solution of isobutanolamine with a mass equivalent to 15% of the mass of thermally isomerized rosin (isobutanolamine/acetone=1:1 g/mL) to form a precipitate, let stand for 2 hours, filter, wash with 50% (v/v) ethanol for three times, and dry to obtain crude ammonium salt of isopimaric acid. Recrystallize each group of crude ammonium salt of isopimaric acid for five times according to multi-recrystallization. During dissolution of ammonium salt of isopimaric acid each time, 95% (v/v) ethanol in 1 to 3 times of the volume is added. During filtration and crystallization, 50% (v/v) ethanol is used for washing. After drying, 25.7 g purified crystal of ammonium salt of isopimaric acid is obtained.

Dissolve all of the purified ammonium salt of isopimaric acid in ether with the same mass, add 1 wt % of hydrochloric acid in batches until the crystal of ammonium salt of isopimaric acid disappears, remove the water layer, wash the ether layer with water a pH of neutral, evaporate ether at one atmosphere and 30° C., dissolve the residue in acetone with a mass of 0.5 times, slowly add water in drops into the solution until precipitated crystals cease to grow, filter and dry to obtain 20.1 g purified isopimaric acid. The yield relative to thermally isomerized rosin is 10.1%.

The operation process of the multi-recrystallization method is shown in FIG. 1, wherein "C" refers to crystallization, "A" refers to the "useful mother liquor" that is left after filtration and crystallization that will be merged and used in the next crystallization process, and "mother liquor" refers to the part that is no longer used and will be discarded. The obtained crude ammonium salt of isopimaric acid is dissolved in organic solvent. The crystal obtained in the first crystallization is C1 and the mother liquor is A1. Mother liquor A1 is concentrated to ½ volume to obtain crystal D1, and the mother liquor is then discarded. Crystal C1 is dissolved and recrystallized to obtain crystal C2. The mother liquor is A2. Crystal D1 is dissolved in mother liquor A2 and then concentrated to ½ volume to obtain crystal D2. The mother liquor is discarded. Crystal C2 is dissolved and recrystallized to obtain crystal C3. The mother liquor is A3. Crystal D2 is dissolved in mother liquor A3 and then concentrated to ½ volume to obtain crystal D3. The mother liquor is discarded. Crystal C3 is dissolved and recrystallized to obtain crystal C4. The mother liquor is A4. Crystal D3 is dissolved in mother liquor A4 and then concentrated to ½ volume to obtain crystal D4. The mother liquor is discarded. Crystal C4 is dissolved and recrystallized to obtain crystal C5. The mother liquor is A5. Crystal D4 is dissolved in mother liquor A5 and then concentrated to ½ volume to obtain crystal D5. The mother liquor is discarded. Crystal C5 and Crystal D5 are merged to obtain purified ammonium salt of isopimaric acid.

Example 8

Dissolve 200 g of the thermally isomerized rosin obtained in Example 2 in acetone with a mass of 11 times, add in drops of an acetone solution of isobutanolamine with a mass equivalent to 21% of the mass of thermally isomerized rosin (isobutanolamine/acetone=1:1 g/mL) to form precipitate, let stand for 2 hours, filter, wash with 50% (v/v) ethanol for three times and dry to obtain crude ammonium salt of isopimaric acid; recrystallize each group of crude ammonium salt of isopimaric acid according to multi-recrystallization for five times. During dissolution of ammonium salt of isopimaric acid each time, 95% (v/v) ethanol in two times of the volume is added. During filtration and crystallization, 50% (v/v) ethanol is used for washing. After drying, purified crystal of ammonium salt of isopimaric acid is obtained.

Dissolve all of the purified ammonium salt of isopimaric acid into ether with a mass of 11 times, add 11 wt % hydrochloric acid in batches until the crystal of ammonium salt of isopimaric acid disappears, remove the water layer and wash the ether layer with water to neutral, evaporate ether at one atmosphere and 40° C., dissolve the residue in acetone with a mass of 3.5 times, add water slowly into the solution in drops until precipitated crystals cease to grow, filter and dry to obtain purified isopimaric acid.

Example 9

Dissolve 200 g of the thermally isomerized rosin obtained in Example 2 into acetone with a mass of 10 times, add in drops of an acetone solution of isobutanolamine equivalent to 40% of the mass of thermally isomerized rosin (isobutanolamine/acetone=1:1 g/mL) to form precipitate, let stand for 2 hours, filter, wash with 50% (v/v) ethanol for three times and dry to obtain crude ammonium salt of isopimaric acid; recrystallize each group of crude ammonium salt of isopimaric acid according to multi-recrystallization for five times. During dissolution of ammonium salt of isopimaric acid each time, 95% (v/v) ethanol in 1~3 times of the volume is added. During filtration and crystallization, 50% (v/v) ethanol is used for washing. After drying, purified crystal of ammonium salt of isopimaric acid is obtained.

Dissolve all of the purified ammonium salt of isopimaric acid in ether with a mass of 20 times, add 20 wt % hydrochloric acid in batches until the crystal of ammonium salt of isopimaric acid disappears, remove the water layer and wash the ether layer with water to neutral, evaporate ether at one atmosphere and 50° C., dissolve the residue into acetone with a mass of 5 times, slowly add water into the solution in drops until precipitated crystals cease to grow, filter and dry to obtain purified isopimaric acid.

Example 10

Dissolve 200 g of the thermally isomerized rosin obtained from Example 6 in acetone with the same mass, add in drops of a solution of acetone isobutanolamine with a mass equivalent to 12% of the mass of the thermally isomerized rosin (isobutanolamine/acetone=1:1 g/mL) to form a precipitate, let stand for 2 hours, filter, wash with 50% (v/v) ethanol for three times and dry to obtain crude ammonium salt of isopimaric acid; recrystallize each group of crude ammonium salt of isopimaric acid according to multi-recrystallization for five times. During dissolution of ammonium salt of isopimaric acid each time, 95% (v/v) ethanol in 1~3 times of the volume is added. During filtration and crystallization, 50% (v/v) ethanol is used for washing. After drying, 24.8 g purified crystal of ammonium salt of isopimaric acid is obtained.

Dissolve all of the purified ammonium salt of isopimaric acid in ether with the same mass, add 1 wt % hydrochloric acid in batches until the crystal of ammonium salt of isopimaric acid disappears, remove the water layer and wash the ether layer with water to neutral, evaporate ether at one atmosphere and 30° C., dissolve the residue in acetone with a mass of 0.5 time, slowly add water into the solution in drops until precipitated crystals cease to grow, filter and dry to obtain 19.8 g purified isopimaric acid. The yield relative to thermally isomerized rosin is 9.9%.

Example 11

The melting point of the product of isopimaric acid obtained in Example 7 and Example 10 is 162° C.~164° C., with a specific rotation $[\alpha]_D^{20}$ at 0° (solvent is 95% ethanol and mass fraction is 2%). The mass fraction of isopimaric acid in the product determined by gas chromatography is 95.4%.

The determined mass of the ion peak of HR-MS:[M-H] is 301.2174 and the calculated value of $[C_{20}H_{29}O_2]^-$ is 301.2168, Δ=0.66 ppm. The determined molecular mass is 302.2248. The given molecular formula is $C_{20}H_{30}O_2$ (DBE=6) and the calculated value is 302.2246.

Figure 2:
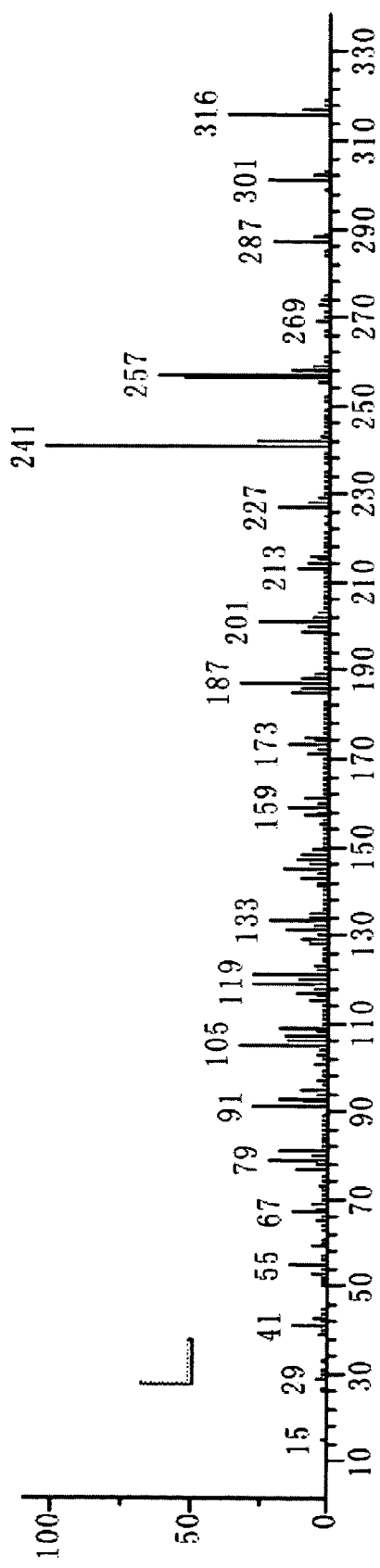
FIG. 2 is a mass spectrometry (MS) analysis spectrogram of the product of isopimaric acid methyl ester.

Mass spectrometry (MS) (see FIG. 2), m/z (peak intensity, %): 316 ($M^+$, molecular ion peak of isopimaric acid methyl ester, $C_{21}H_{32}O_2$, 35.5), 301 (M-Me, 21), 287 (M-$CH_2$=$CH_2$+H, 20), 257 (M-MeCO$_2$, 59.7), 256 (M-CO$_2$Me, 50.7) 242 (25.3), 241 (100, M-Me-HCO$_2$CH$_3$), 227 (20), 187 (30.2), 119 (26.3), 121 (25.8), 105 (30.3), and 91 (25.7). The detection result of the MS database is consistent with the standard spectrum of isopimaric acid.

Figure 3:
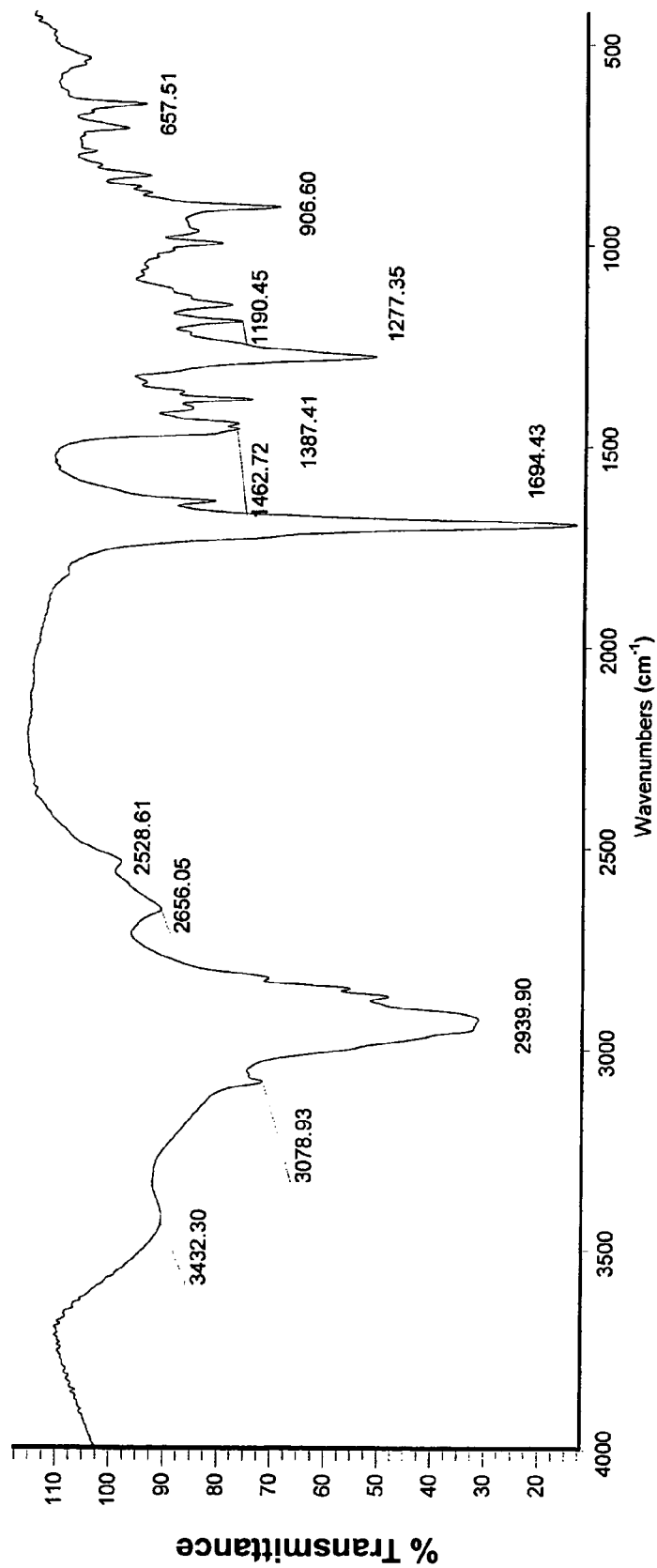
FIG. 3 is an infrared (IR) analysis spectrogram of the product of isopimaric acid.

Infrared (IR) (KBr pellet method, the spectrum is shown in FIG. 3), (cm$^{-1}$): 3432 (moderately strong, wide peak, OH), 3079 (C=C—H), 2940 (C—H), 2656, 2528, 1694 (strong, C=O), 1463, 1387 (CH$_3$), 1277 (C—O), 1190, 906 (C=C—H), 658.

Figure 4:
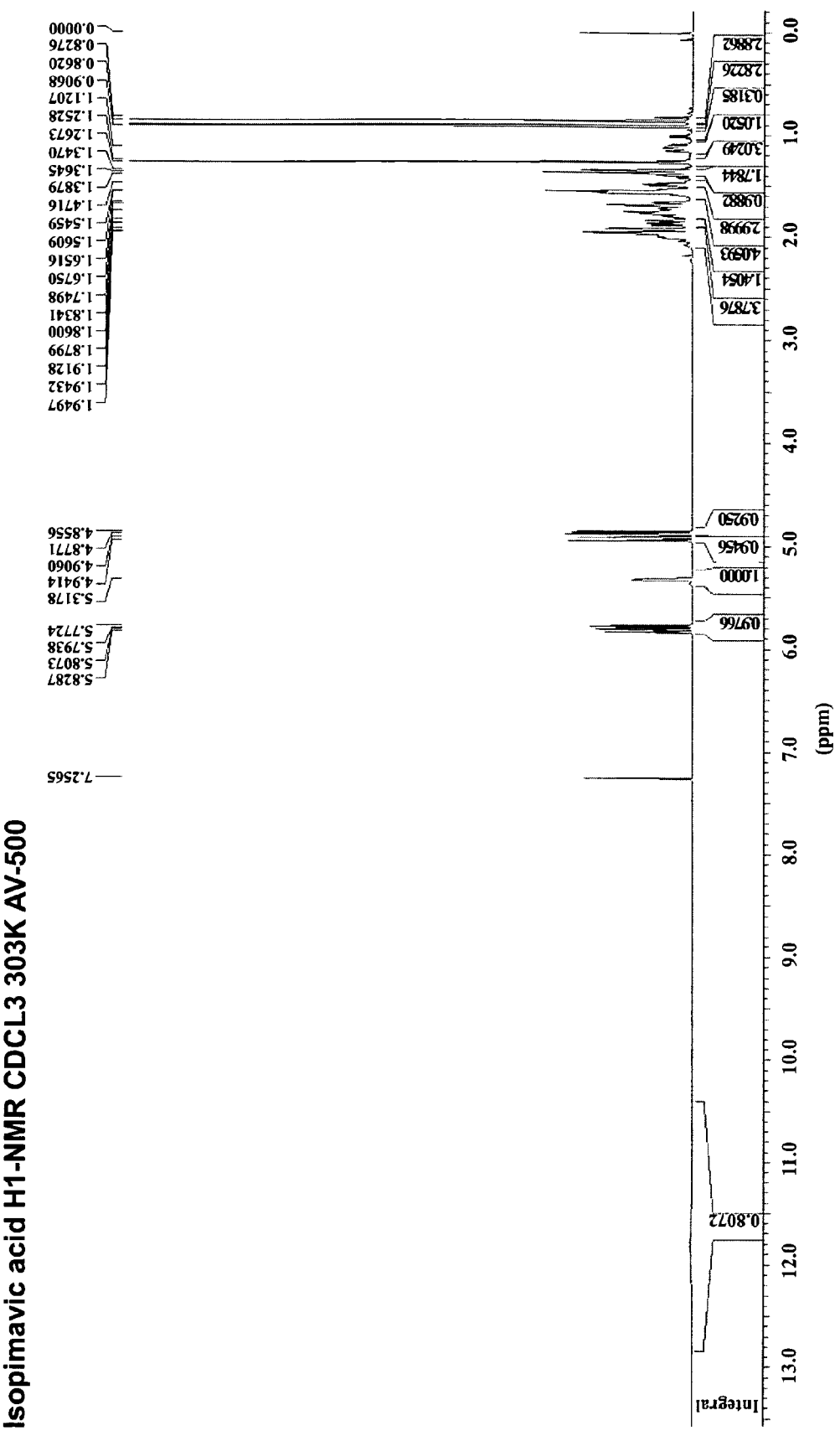
FIG. 4 is a PNMR analysis spectrogram of the product of isopimaric acid.

$^1$HNMR (see FIG. 4, CDCl$_3$), δ(ppm): 0.8620 (s, 3H, $C_{10}$—CH$_3$), 0.9068 (s, 3H, $C_{13}$—CH$_3$), 1.2673 (s, 3H, $C_4$—CH$_3$), 1.085~1.146 (m, 1H), 1.3216~1.4138 (m, 2H), 1.4716~1.4891 (m, 1H), 1.5250~1.5800 (m, 3H), 4.8651 (dd, 1H, $J_1$=10.70 Hz, $J_3$=1.25 Hz, CH), 4.9251 (dd, 1H, $J_2$=17.50 Hz, $J_3$=1.25 Hz, CH), 5.322 (dd, J=7.45 Hz, 1H, C=CH), 5.801 (dd, 1H, $J_1$=10.70 Hz, $J_2$=17.50 Hz, CH), 11.6~12.2 (broad s, 1H, COOH).

Through the analysis results of the physical properties, MS, IR and PNMR of this product, the chemical structure of isopimaric acid is exactly identified.

Comparison 1

Dissolve 200 g *Pinus elliottii* rosin in 400 mL of n-heptane, add 15 g piperidine, stir, cool the solution to room temperature, cool it in a refrigerator for 2 hours, keep stirring the solution until it has resumed to normal temperature, then put the mixture into a refrigerator and freeze it overnight to separate ammonium salt, use 95% ethanol as solvent and recrystallize ammonium salt of isopimaric acid according to multi-recrystallization for five times to obtain 25 g ammonium salt.

Dissolve the ammonium salt in 100 mL ether, add 1 wt %~20 wt % hydrochloric acid until crystal of ammonium salt of isopimaric acid disappears. Remove the water layer, wash the ether layer with water to neutral, evaporate ether at one atmosphere and at 30° C.~50° C., dissolve the residue in acetone with a mass of 0.5~5 times, add distilled water slowly into the solution in drops until precipitated crystals cease to grow, filter and dry to obtain 8.2 g pure isopimaric acid. The yield is 4.1%. The purity of isopimaric acid determined by gas chromatography is 87%.

Example 12

The method in Example 2 is adopted, wherein isobutanolamine is replaced with piperidine. A theoretical amount of isobutanolamine and piperidine are respectively added into an equivalent amount of rosin. When isobutanolamine is used, acetone is the recrystallization solvent; and when piperidine is used, n-heptane is the recrystallization solvent. The results are shown in Table 1.

TABLE 1

Comparison of Separation and Purification Effect Between the Isobutanolamine Method and the Piperidine Method

| Item | Isobutanolamine Method | Piperidine Method |
|---|---|---|
| Thermally isomerized rosin (g) | 200 | 200 |
| Addition of organic amine (g) | 14 | 15 |
| Reaction time (h) | 2 | 2 |
| Isopimaric acid product (g) | 20.1 | 8.2 |
| Product yield (%) | 10.1 | 4.1 |
| Product purity (%) | 95.4 | 87.0 |

Example 13

The method in Example 2 is adopted, wherein the 95% ethanol multi-recrystallization of crude ammonium salt of isopimaric acid is replaced with thrice-recrystallization with 95% (v/v) ethanol, methyl acetate, methyl acetate-anhydrous ethanol (2:3, v/v), anhydrous ethanol, methanol or other solvents. The same treatment by the method described in Example 1 is adopted to obtain purified isopimaric acid. The comparison of recrystallization effect among different recrystallization solvents is shown in Table 2.

TABLE 2

Effect Comparison of Different Recrystallization Solvents

| Recrystallization Solvent | Yield of isopimaric acid (relative to thermally isomerized rosin, %) | GC purity of isopimaric acid (%) |
|---|---|---|
| 95% (v/v) ethanol | 27.2 | 79.07 |
| Methyl acetate-anhydrous ethanol | 23.2 | 75.34 |
| Methyl acetate | 28.4 | 67.45 |
| Anhydrous ethanol | 18.2 | 80.10 |
| Methanol | 12.0 | 9.21 |

Note:
The yield of isopimaric acid is the calculated mass fraction relative to thermally isomerized rosin.

What is claimed is:
1. A process for preparing Compound I, the process comprising:

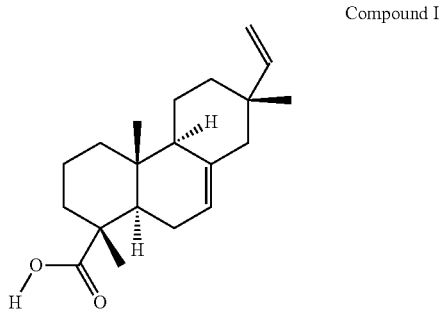

Compound I dissolving thermally isomerized rosin in acetone having a total mass of 1-10 times the mass of the rosin,
adding dropwise to the dissolved rosin an amount of an acetone solution of isobutanolamine (acetone/isobutanolamine=(1:1 mL/g)) to form a precipitate, wherein the amount of the acetone solution is 10-40% by weight of thermally isomerized rosin,
standing, filtering, washing with 50% (v/v) ethanol, and drying the precipitate to obtain a crude ammonium salt of Compound I;

recrystallizing the crude ammonium salt at least five times, and drying to obtain purified crystal of the ammonium salt of Compound I;

dissolving the purified crystal in ether of 1-20 times the mass of the purified crystal, adding a solution of 1-20% (wt/wt) hydrochloric acid to the dissolved crystal until the crystal disappears, removing the water layer and washing the ether layer with water to neutral, evaporating the ether at one atmosphere and 30-50° C. to obtain a residue, dissolving the residue in acetone of 0.5-5 times the mass of the residue, adding water slowly into the solution in drops until precipitated crystals cease to grow, and filtering and drying the precipitated crystals to obtain purified Compound I.

2. The process according to claim 1, wherein the thermally isomerized rosin is prepared by a method comprising:

evaporating water from pine oleoresin that contains Compound I at one atmosphere and 90-114° C., evaporating turpentine from the dried oleoresin at 10–50 kPa and 140-170° C., isomerizing the rosin at 150-180° C. for 1-3 h, and filtering and cooling the isomerized rosin to room temperature to obtain thermally isomerized rosin.

3. The process according to claim 2, wherein the pine oleoresin that contains Compound I is *Pinus elliottii* pine oleoresin, *Pinus caribaea* pine oleoresin, *Pinus Khasya* pine oleoresin or *Pinus massoniana* pine oleoresin.

4. The process according to claim 1, wherein the thermally isomerized rosin is obtained through isomerizing rosin at 150-180° C. for 1-3 h, filtering, and cooling to room temperature.

5. The process according to claim 4, wherein the rosin is *Pinus elliottii* rosin, *Pinus caribaea* pine oleoresin, *Pinus Khasya* pine oleoresin or *Pinus massoniana* pine oleoresin.

6. The process according to claim 1, wherein the solvent used in recrystallizing is 95% (v/v) ethanol, methyl acetate, methyl acetate-anhydrous ethanol, anhydrous ethanol or methanol.

* * * * *